United States Patent
Lin et al.

(10) Patent No.: US 7,615,353 B1
(45) Date of Patent: Nov. 10, 2009

(54) TIVOZANIB RESPONSE PREDICTION

(75) Inventors: Jie Lin, W. Roxbury, MA (US); Murray Robinson, Boston, MA (US); Bin Feng, N. Reading, MA (US); Wenping Kathryn Sun, Cambridge, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/498,183

(22) Filed: Jul. 6, 2009

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.31; 536/24.33

(58) Field of Classification Search .................. None
See application file for complete search history.

(56) References Cited

U.S. PATENT DOCUMENTS

2007/0264193 A1   11/2007   Shojaei et al.

FOREIGN PATENT DOCUMENTS

WO   WO-2007/028005   3/2007
WO   WO-2008/128008   10/2008

OTHER PUBLICATIONS

Arao et al., 2005, *Int J. Cancer* 118:483-489.
Ayers et al., "Discovery and Validation of Biomarkers that Respond to Treatment with Brivanib Alaninate, a Small-Molecule VEGFR-2/FGFR-1 Antagonist," 2004, *Cancer Research* 64:7857-7866.
Duncan et al., 2008, *Clin. Cancer Res.* 14:3030-3035.
Golshayan et al., "Predicting outcome to VEGF-targeted therapy in metastatic clear-cell renal cell carcinoma: data from recent studies," 2008, Future Oncol. 4:85-92.
Longo et al., "Anti-VEGF therapy: the search for clinical biomarkers," 2008, *Expert Rev. Mol. Diag.* 8:301-314.
Murdoch et al., "The role of myeloid cells in the promotion of tumour angiogenesis," 2008, *Nature Reviews Cancer* 8:618-631.
Shojaei et al., "G-CSF-initiated myeloid cell mobilization and angiogenesis mediate tumor refractoriness to anti-VEGF therapy in mouse models," 2009, *Proc. Nat'l. Acad. Sci. USA* 106:6742-6747.
Shojaei et al., "Tumor refractoriness to anti-VEGF treatment is mediated by $CD11b^+Gr1^+$ myeloid cells," 2007, *Nature Biotechnology* 25:911-920.

*Primary Examiner*—Gary Benzion
*Assistant Examiner*—Samuel Woolwine
(74) *Attorney, Agent, or Firm*—Gary L. Creason

(57) ABSTRACT

A diagnostic method for predicting quantitatively whether a human tumor will be responsive or resistant (non-responsive) to treatment with the VEGF inhibitor, tivozanib (AV-951), is disclosed. The test is based on application of an algorithm to measurements of expression levels of the genes in a predictive gene set.

6 Claims, 2 Drawing Sheets

TIVOZANIB RESPONSE PREDICTION

FIELD OF THE INVENTION

The field of the invention is molecular biology, genetics, oncology, bioinformatics and clinical diagnostics.

BACKGROUND OF THE INVENTION

Most cancer drugs are effective in some patients, but not others. This results from genetic variation among tumors, and can be observed even among tumors within the same patient. Variable patient response is particularly pronounced with respect to targeted therapeutics. Therefore, the full potential of targeted therapies cannot be realized without suitable tests for determining which patients will benefit from which drugs. According to the National Institutes of Health (NIH), the term "biomarker" is defined as "a characteristic that is objectively measured and evaluated as an indicator of normal biologic or pathogenic processes or pharmacological response to a therapeutic intervention."

The development of improved diagnostics based on the discovery of biomarkers has the potential to accelerate new drug development by identifying, in advance, those patients most likely to show a clinical response to a given drug. This would significantly reduce the size, length and cost of clinical trials. Technologies such as genomics, proteomics and molecular imaging currently enable rapid, sensitive and reliable detection of specific gene mutations, expression levels of particular genes, and other molecular biomarkers. In spite of the availability of various technologies for molecular characterization of tumors, the clinical utilization of cancer biomarkers remains largely unrealized because few cancer biomarkers have been discovered. For example, a recent review article states:

There is a critical need for expedited development of biomarkers and their use to improve diagnosis and treatment of cancer. (Cho, 2007, *Molecular Cancer* 6:25)

Another recent review article on cancer biomarkers contains the following comments:

The challenge is discovering cancer biomarkers. Although there have been clinical successes in targeting molecularly defined subsets of several tumor types—such as chronic myeloid leukemia, gastrointestinal stromal tumor, lung cancer and glioblastoma multiforme—using molecularly targeted agents, the ability to apply such successes in a broader context is severely limited by the lack of an efficient strategy to evaluate targeted agents in patients. The problem mainly lies in the inability to select patients with molecularly defined cancers for clinical trials to evaluate these exciting new drugs. The solution requires biomarkers that reliably identify those patients who are most likely to benefit from a particular agent. (Sawyers, 2008, *Nature* 452:548-552, at 548)

Comments such as the foregoing illustrate the recognition of a need for the discovery of clinically useful biomarkers and diagnostic methods based on such biomarkers.

There are three distinct types of cancer biomarkers: (1) prognostic biomarkers, (2) predictive biomarkers, and (3) pharmacodynamic (PD) biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2 or NEU) gene is amplified are likely to benefit from treatment with trastuzumab (HERCEPTIN®), whereas patients without ERBB2 gene amplification are unlikely to benefit from treatment with trastuzumab. A PD biomarker is an indication of the effect(s) of a drug on a patient while the patient is taking the drug. Accordingly, PD biomarkers often are used to guide dosage level and dosing frequency, during the early stages of clinical development of a new drug. For a discussion of cancer biomarkers, see, e.g., Sawyers, 2008, *Nature* 452:548-552.

Tivozanib (also known as AV-951) is a potent and selective small-molecule inhibitor of VEGF receptors 1, 2 and 3. Tivozanib exhibits picomolar inhibitory activity against all three receptors, and it exhibits antitumor activity in preclinical models (Nakamura et al., 2006, *Cancer Res.* 66:9134-9142). Tivozanib has yielded positive interim results in a 272-patient Phase 2 clinical trial (Bhargava et al., 2009, *ASCO Genitourinary Cancers Symposium*, Abstract No. 283).

Despite a large amount of pre-clinical and clinical research focused on VEGF-targeted therapy, the mechanisms responsible for the anti-tumor activity of anti-VEGF agents are not fully understood. As with other types of targeted therapy, some, but not all, patients benefit from tivozanib therapy. The complexity of VEGF biology makes the effectiveness of tivozanib against any given tumor unpredictable. Therefore, there is a need for diagnostic methods based on predictive biomarkers that can be used to identify patients with tumors that are likely (or unlikely) to respond to treatment with tivozanib.

SUMMARY OF THE INVENTION

The invention is based on the discovery of a set of genes: (a) that display coherence in their expression levels in mice and humans; and (b) whose individual expression levels collectively indicate whether a mouse tumor or human tumor is likely to be responsive (sensitive) or non-responsive (resistant) to treatment with the anti-cancer drug known as tivozanib. Accordingly, the invention provides a diagnostic method for predicting quantitatively whether a human tumor will be responsive or non-responsive to treatment with tivozanib. The method includes the following steps:

(a) measuring, in a tissue sample from a human tumor, the relative expression level of each gene in a predictive gene set (PGS), wherein the PGS consists essentially of the following genes (denoted by the HUGO gene symbol):

AIF1
APBB1IP
CCR1
CLEC7A
CSF1R
CSF2RB
CTSS
CYBB
EVI2A
EVI2B
GMFG
HCK
HCLS1
HLA-DMA
IL10RA
ITGB2
LAIR1
LCP1
LCP2
LILRB1
LILRB2

LST1
LY86
MNDA
MS4A6A
MYO1F
NCF4
SLA
SLAMF8
TLR1
TYROBP
PLEK
CYTH4 and
PTPRC; and (b) calculating a PGS score according to the following algorithm:

$$PGS.\text{score} = \frac{1}{42} * \sum_{i=1}^{42} Ei$$

wherein E1, E2, . . . E42 are the expression values of the 42 genes in the PGS.

A PGS score below a defined threshold indicates that the tumor is likely to be responsive to tivozanib, and a PGS score above a defined threshold indicates that the tumor is likely to be non-responsive to tivozanib.

Some embodiments of the invention include performing a threshold determination analysis, thereby generating a defined threshold. The threshold determination analysis can include a receiver operator characteristic curve analysis. The relative gene expression level for each gene in the PGS can be obtained by measuring the mRNA level for that gene. Suitable methods for measuring mRNA levels in tumor tissue samples include DNA microarray analysis and quantitative reverse transcriptase polymerase chain reaction (qRT-PCR), e.g., TAQMAN® assays.

In another aspect, the invention provides a PCR primer set comprising a primer pair for measuring expression of each of the genes in a human PGS or a mouse PGS. The invention also provides a diagnostic test kit comprising such a PCR primer set.

DETAILED DESCRIPTION OF THE INVENTION

Figure 1:
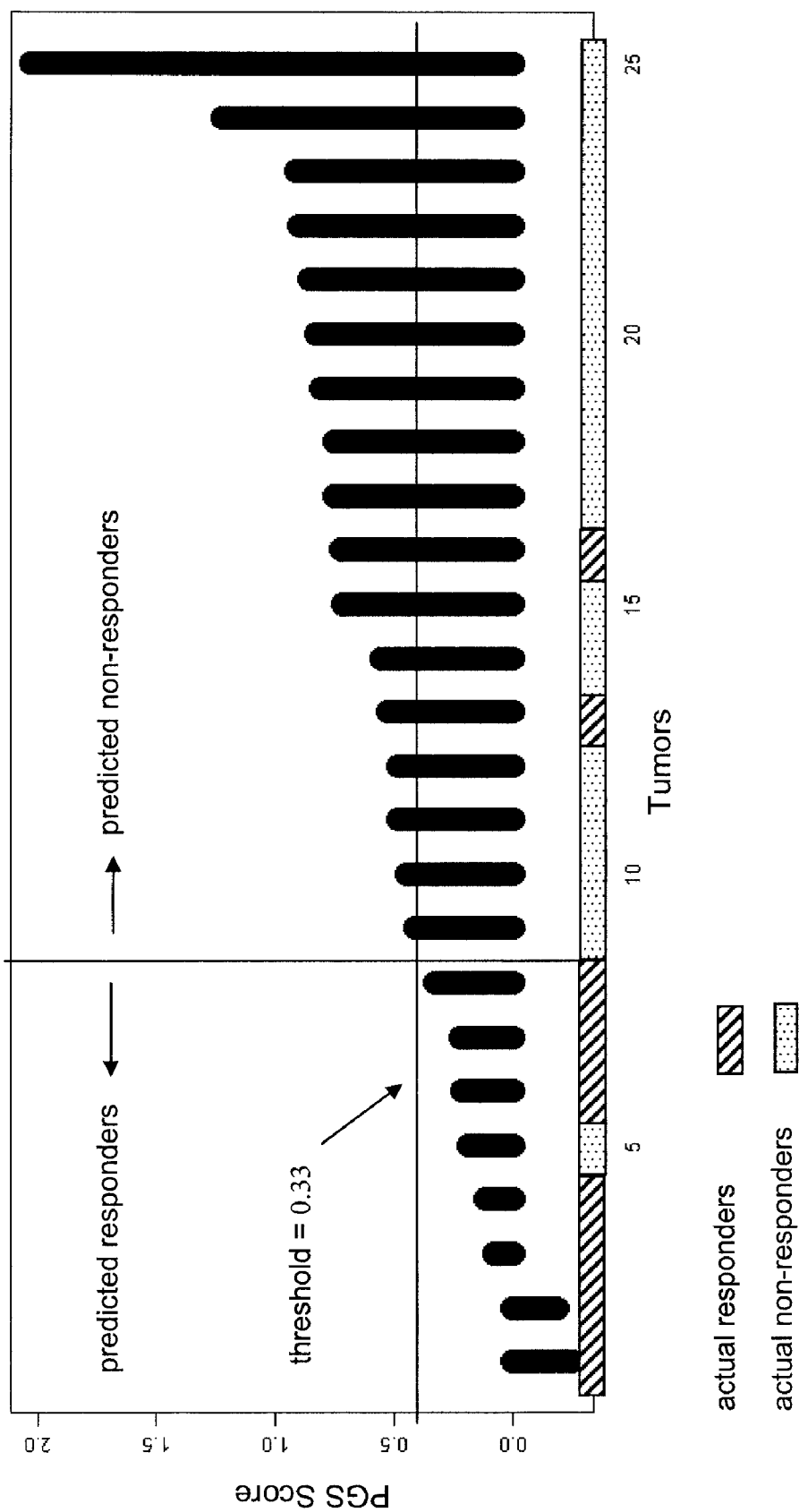
FIG. 1 is a waterfall plot showing the PGS score for each of 25 mouse tumors (HER2-driven breast tumors), arranged by PGS score, low to high, with response or non-response to tivozanib (AV-591) treatment indicated below each tumor. Cross-hatching indicates responsive tumor; no cross-hatching indicates non-responsive tumor.

The individual expression levels of the genes of the PGS can be used collectively as predictive biomarkers for classifying mouse tumors and human tumors according to their likelihood of responding to treatment with the anti-tumor drug known as tivozanib. Such classification of tumors is useful for identifying human patients who are suitable candidates for treatment with tivozanib in a clinical setting.

DEFINITIONS

As used herein, "AV-951" and "tivozanib" mean N-{2-chloro-4-[(6,7-dimethoxy-4-quinolyl)oxy]-phenyl}-N'-(5-methyl-3-isoxazolyl)urea, which has the following chemical structure, including salts and polymorphs thereof:

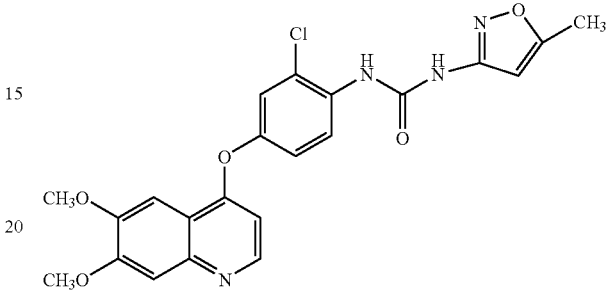

As used herein, "coherence" means, when applied to a set of genes, that expression levels of the members of the set display a statistically significant tendency to increase or decrease in concert, within a given type of tissue, e.g., tumor tissue. Without intending to be bound by theory, the inventors note that coherence is likely to indicate that the coherent genes share a common involvement in one or more biological functions.

As used herein, "optimum threshold PGS score" means the threshold PGS score at which the classifier gives the most desirable balance between the cost of false negative calls and false positive calls.

As used herein, "PGS Score" means the numerical value calculated using following algorithm:

$$PGS.\text{score} = \frac{1}{42} * \sum_{i=1}^{42} Ei$$

wherein E1, E2, . . . E42 are the expression values of the 42 genes in the PGS.

As used herein, "receiver operating characteristic" (ROC) curve means a graphical plot of false positive rate (sensitivity) versus true positive rate (specificity) for a binary classifier system. In construction of an ROC curve, the following definitions apply:

False negative rate:FNR=1−TPR

True positive rate:TPR=true positive/(true positive+ false negative)

False positive rate:FPR=false positive/(false positive+ true negative)

As used herein, "response" or "responding" to treatment means, with regard to a treated tumor, that the tumor displays: (a) slowing of growth, (b) cessation of growth, or (c) regression.

As used herein, "threshold determination analysis" means analysis of a dataset representing a given tumor type, e.g., human renal cell carcinoma, to determine a threshold PGS score, e.g., an optimum threshold PGS score, for that particular tumor type. In the context of a threshold determination analysis, the dataset representing a given tumor type includes (a) actual response data (response or non-response), and (b) a PGS score for each tumor from a group of tumor-bearing mice or humans.

Predictive Gene Set (PGS)

In embodiments of the invention involving identification of human tumors likely to be responsive or non-responsive to treatment with tivozanib, the PGS consists of, or consists essentially of, the 42 human genes listed in Table 1 (below):

TABLE 1

| Human Gene | HUGO Symbol | Entrez GeneID |
|---|---|---|
| 1 | AIF1 | 199 |
| 2 | APBB1IP | 54518 |
| 3 | ARHGAP30 | 257106 |
| 4 | C3AR1 | 719 |
| 5 | CCR1 | 1230 |
| 6 | CD37 | 951 |
| 7 | CD53 | 963 |
| 8 | CD86 | 942 |
| 9 | CLEC7A | 64581 |
| 10 | CSF1R | 1436 |
| 11 | CSF2RB | 1439 |
| 12 | CTSS | 1520 |
| 13 | CYBB | 1536 |
| 14 | DOCK2 | 1794 |
| 15 | EVI2A | 2123 |
| 16 | EVI2B | 2124 |
| 17 | FPR3 | 2359 |
| 18 | GMFG | 9535 |
| 19 | GPR65 | 8477 |
| 20 | HCK | 3055 |
| 21 | HCLS1 | 3059 |
| 22 | HLA-DMA | 3108 |
| 23 | IL10RA | 3587 |
| 24 | ITGB2 | 3689 |
| 25 | LAIR1 | 3903 |
| 26 | LCP1 | 3936 |
| 27 | LCP2 | 3937 |
| 28 | LILRB1 | 10859 |
| 29 | LILRB2 | 10288 |
| 30 | LST1 | 7940 |
| 31 | LY86 | 9450 |
| 32 | MNDA | 4332 |
| 33 | MS4A6A | 64231 |
| 34 | MYO1F | 4542 |
| 35 | NCF4 | 4689 |
| 36 | SLA | 6503 |
| 37 | SLAMF8 | 56833 |
| 38 | TLR1 | 7096 |
| 39 | TYROBP | 7305 |
| 40 | PLEK | 5341 |
| 41 | CYTH4 | 27128 |
| 42 | PTPRC | 5788 |

Tissue Sample

A tissue sample from a tumor in a human patient or a mouse model can be used as a source of RNA so that the PGS gene expression levels in the sample can be determined in accordance with the present invention. Typically, the tumor is a carcinoma, sarcoma, glioma or lymphoma. The tissue sample can be obtained by using conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by one of skill in the art to obtain tumor samples for use in practicing the invention. The tumor tissue sample should be large enough to provide sufficient RNA for measuring individual gene expression levels.

The tumor tissue sample can be in any form that allows gene expression analysis, e.g., RNA extraction and quantitation. Accordingly, the tissue sample can be fresh, preserved through suitable cryogenic techniques, or preserved through non-cryogenic techniques. A standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation and tissue preservation for subsequent RNA extraction are well-known to those of skill in the art.

Individual gene expression levels for each gene in the PGS are the input values used to calculate the PGS score. Once a tissue sample is obtained it is necessary to determine, i.e., measure, the expression levels of the individual genes in the PGS. Gene expression level can be determined by any suitable method. Two exemplary methods for measuring individual expression are DNA microarray analysis and qRT-PCR, which are discussed below. A prerequisite for either of these alternative methods is RNA isolation.

RNA Isolation

Methods for rapid and efficient extraction of eukaryotic mRNA, i.e., poly(a) RNA, from tissue samples are well established and known to those of skill in the art. See, e.g., Ausubel et al., 1997, *Current Protocols of Molecular Biology*, John Wiley & Sons. The tissue sample can be fresh, frozen or fixed paraffin-embedded (FFPE) clinical study tumor specimens. In general, RNA isolated from fresh or frozen tissue samples tends to be less fragmented than RNA from FFPE samples. FFPE samples of tumor material, however, are more readily available, and FFPE samples are suitable sources of RNA for use in methods of the present invention. For a discussion of FFPE samples as sources of RNA for gene expression profiling by RT-PCR, see, e.g., Clark-Langone et al., 2007, *BMC Genomics* 8:279. Also see, De Andrés et al., 1995, *Biotechniques* 18:42044; and Baker et al., U.S. Patent Application Publication No. 2005/0095634. The use of commercially available kits with vendor's instructions for RNA extraction and preparation is widespread and common. Commercial vendors of various RNA isolation products and complete kits include Qiagen (Valencia, Calif.), Invitrogen (Carlsbad, Calif.), Ambion (Austin, Tex.) and Exiqon (Woburn, Mass.).

In general, RNA isolation begins with tissue/cell disruption. During tissue/cell disruption it is desirable to minimize RNA degradation by RNases. One approach to limiting RNase activity during the RNA isolation process is to ensure that a denaturant is in contact with cellular contents as soon as the cells are disrupted. Another common practice is to include one or more proteases in the RNA isolation process. Optionally, fresh tissue samples are immersed in an RNA stabilization solution, at room temperature, as soon as they are collected. The stabilization solution rapidly permeates the cells, stabilizing the RNA for storage at 4° C., for subsequent isolation. One such stabilization solution is available commercially as RNAlater® (Ambion, Austin, Tex.).

In some protocols, total RNA is isolated from disrupted tumor material by cesium chloride density gradient centrifugation. In general, mRNA makes up approximately 1% to 5% of total cellular RNA. Immobilized Oligo(dT), e.g., oligo(dT) cellulose, is commonly used to separate mRNA from ribosomal RNA and transfer RNA. If stored after isolation, RNA must be stored in under RNase-free conditions. Methods for stable storage of isolated RNA are known in the art. Various commercial products for stable storage of RNA are available.

Microarray Analysis

The mRNA expression level for multiple genes can be measured using conventional DNA microarray expression profiling technology. A DNA microarray is a collection of specific DNA segments or probes affixed to a solid surface or substrate such as glass, plastic or silicon, with each specific DNA segment occupying a known location in the array. Hybridization with a sample of labeled RNA, usually under stringent hybridization conditions, allows detection and quantitation of RNA molecules corresponding to each probe in the array. After stringent washing to remove non-specifically bound sample material, the microarray is scanned by confocal laser microscopy or other suitable detection method. Modern commercial DNA microarrays, often known as DNA chips, typically contain tens of thousands of probes, and thus can measure expression of tens of thousands of genes simultaneously. Such microarrays can be used in practicing the present invention. Alternatively, custom chips containing as few probes as those needed to measure expression of the genes of the PGS, plus necessary controls or standards (for data normalization, etc.), can be used in practicing the invention.

To facilitate data normalization, a two-color microarray reader can be used. In a two-color (two-channel) system, samples are labeled with a first fluorophore that emits at a first wavelength, while an RNA or cDNA standard is labeled with a second fluorophore that emits at a different wavelength. For example, Cy3 (570 nm) and Cy5 (670 nm) often are employed together in two-color microarray systems.

DNA microarray technology is well-developed, commercially available, and widely employed. Therefore, in performing methods of the invention, a person of ordinary skill in the art can use microarray technology to measure expression levels of genes in the PGS without undue experimentation. DNA microarray chips, reagents (such as those for RNA or cDNA preparation, RNA or cDNA labeling, hybridization and washing solutions), instruments (such as microarray readers) and protocols are well known in the art and available from various commercial sources. Commercial vendors of microarray systems include Agilent Technologies (Santa Clara, Calif.) and Affymetrix (Santa Clara, Calif.), but other PCR systems can be used.

Quantitative RT-PCR

The level of mRNA representing individual genes in the PGS can be measured using conventional quantitative reverse transcriptase polymerase chain reaction (qRT-PCR) technology. Advantages of qRT-PCR include sensitivity, flexibility, quantitative accuracy, and ability to discriminate between closely related mRNAs. Guidance concerning the processing of tissue samples for quantitative PCR is available from various sources, including manufacturers and vendors of commercial products for qRT-PCR (e.g., Qiagen (Valencia, Calif.) and Ambion (Austin, Tex.)). Instrument systems for automated performance of qRT-PCR are commercially available and used routinely in many laboratories. An example of a well-known commercial system is the Applied Biosystems 7900HT Fast Real-Time PCR System (Applied Biosystems, Foster City, Calif.).

Once isolated mRNA is in hand, the first step in gene expression profiling by RT-PCR is the reverse transcription of the mRNA template into cDNA, which is then exponentially amplified in a PCR reaction. Two commonly used reverse transcriptases are avilo myeloblastosis virus reverse transcriptase (AMV-RT) and Moloney murine leukemia virus reverse transcriptase (MMLV-RT). The reverse transcription reaction typically is primed with specific primers, random hexamers, or oligo(dT) primers. Suitable primers are commercially available, e.g., GeneAmp® RNA PCR kit (Perkin Elmer, Waltham, Mass.). The resulting cDNA product can be used as a template in the subsequent polymerase chain reaction.

The PCR step is carried out using a thermostable DNA-dependent DNA polymerase. The polymerase most commonly used in PCR systems is a *Thermus aquaticus* (Taq) polymerase. The selectivity of PCR results from the use of primers that are complementary to the DNA region targeted for amplification, i.e., regions of the cDNAs reverse transcribed from the genes of the PGS. Therefore, when qRT-PCR is employed in the present invention, primers specific to each gene in the PGS are based on the cDNA sequence of the gene. Commercial technologies such as SYBR® green or TaqMan® (Applied Biosystems, Foster City, Calif.) can be used in accordance with the vendor's instructions. Messenger RNA levels can be normalized for differences in loading among samples by comparing the levels of housekeeping genes such as beta-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA.

Suitable primer sets for PCR analysis of expression levels of the genes in the PGS can be designed and synthesized by one of skill in the art, without undue experimentation. Alternatively, complete PCR primer sets for practicing the present invention can be purchased from commercial sources, e.g., Applied Biosystems, based on the identities of the genes in the PGS, as set forth above in Table 1. PCR primers preferably are about 17 to 25 nucleotides in length. Primers can be designed to have a particular melting temperature (Tm), using conventional algorithms for Tm estimation. Software for primer design and Tm estimation are available commercially, e.g., Primer Express™ (Applied Biosystems), and also are available on the internet, e.g., Primer3 (Massachusetts Institute of Technology). By applying established principles of PCR primer design, a large number of different primers can be used to measure the expression level of any given gene. Accordingly, the invention is not limited with respect to which particular primers are used for any given gene in the PGS.

PGS Score Interpretation

PGS scores are interpreted with respect to a threshold PGS score. In the present invention, PGS scores higher than the threshold PGS score will be interpreted as indicating a tumor likely to be non-responsive (resistant) to tivozanib treatment. PGS scores lower than the threshold PGS score will be interpreted as indicating a tumor likely to be responsive (sensitive) to tivozanib treatment. It is contemplated that a given threshold PGS score will vary depending on tumor type. In the context of the present invention, the term "tumor type" takes into account (a) species (mouse or human); and (b) organ or tissue of origin. Optionally, tumor type further takes into account tumor categorization based on gene expression characteristics, e.g., HER2-positive breast tumors, or non-small cell lung tumors expressing a particular EGFR mutation.

For any given tumor type, an optimum threshold PGS score can be determined (or at least approximated) empirically by performing a threshold determination analysis. Preferably, threshold determination analysis includes receiver operator characteristic (ROC) curve analysis.

ROC curve analysis is an established statistical technique, the application of which is within ordinary skill in the art. For a discussion of ROC curve analysis, see generally Zweig et al., 1993, "Receiver operating characteristic (ROC) plots: a fundamental evaluation tool in clinical medicine," *Clin. Chem.* 39:561-577; and Pepe, 2003, *The statistical evaluation of medical tests for classification and prediction*, Oxford Press, New York.

PGS scores and the optimum threshold PGS score may vary from tumor type to tumor type. Therefore, a threshold determination analysis preferably is performed on one or more datasets representing any given tumor type to be tested using the present invention. The dataset used for threshold determination analysis includes: (a) actual response data (response or non-response), and (b) a PGS score for each tumor sample from a group of human tumors or mouse tumors. Once a PGS score threshold is determined with respect to a given tumor type, that threshold can be applied to interpret PGS scores from tumors of that tumor type.

The ROC curve analysis is performed essentially as follows. Any sample with a PGS score greater than threshold is identified as a non-responder. Any sample with a PGS score less than or equal to threshold is identified as responder. For every PGS score from a tested set of samples, "responders" and "non-responders" (hypothetical calls) are classified using that PGS score as the threshold. This process enables calculation of TPR (y vector) and FPR (x vector) for each potential threshold, through comparison of hypothetical calls against the actual response data for the data set. Then an ROC curve is constructed by making a dot plot, using the TPR vector, and FPR vector. If the ROC curve is above the diagonal from (0, 0) point to (1.0, 0.5) point, it shows that the PGS test result is a better test than random (see, e.g., FIG. 2).

The ROC curve can be used to identify the best operating point. The best operating point is the one that yields the best balance between the cost of false positives weighed against the cost of false negatives. These costs need not be equal. The average expected cost of classification at point x,y in the ROC space is denoted by the expression $$C=(1-p)\text{alpha}*x+p*\text{beta}(1-y)$$

wherein:

alpha=cost of a false positive, beta=cost of missing a positive (false negative), and p=proportion of positive cases.

False positives and false negatives can be weighted differently by assigning different values for alpha and beta. For example, if it is decided to include more patients in the responder group at the cost of treating more patients who are non-responders, one can put more weight on alpha. In this case, it is assumed that the cost of false positive and false negative is the same (alpha equals to beta). Therefore, the average expected cost of classification at point x,y in the ROC space is:

$$C'=(1-p)*x+p*(1-y).$$

The smallest C' can be calculated after using all pairs of false positive and false negative (x, y). The optimum PGS score threshold is calculated as the PGS score of the (x, y) at C'. For example, as shown in Example 4, the optimum PGS score threshold, as determined using this approach, was found to be 0.33.

In addition to predicting whether a tumor will be responsive or resistant to treatment with tivozanib, a PGS score provides an approximate, but useful, indication of how likely a tumor is to be responsive or non-responsive. In general, the lower the PGS score, the more likely a tumor is to be responsive to tivozanib, and the higher the PGS score, the more likely a tumor is to be resistant to tivozanib.

Test Kits

The invention includes a diagnostic test kit comprising certain components for performing methods of the invention. A diagnostic test kit enhances convenience, speed and reproducibility in the performance of diagnostic assays.

For example, in an exemplary qRT-PCR-based embodiment of the invention, a basic diagnostic test kit includes PCR primers for all the members of a PGS according to the present invention. In other embodiments, a more elaborate test kit contains not only PCR primers, but also buffers, reagents and detailed instructions for measuring the expression levels of the members of a PGS, using PCR technology. In a preferred embodiment, the kit includes a test protocol and all the consumable components needed for the test, except the RNA sample(s).

In an exemplary DNA microarray-based embodiment of the invention, a test kit includes a micro fluidic card (array) designed for use with a particular instrument. Optionally, the micro fluidic card is a custom made device designed specifically for simultaneous measurement of the expression of the PGS set forth above in Table 1. Such custom micro fluidic cards are commercially available. For example, the TaqMan Array is a 384-well micro fluidic card (array) designed for use with the Applied Biosystems 7900HT Fast Real Time PCR System (Applied Biosystems, Foster City, Calif.). Some embodiments of the invention involve a custom DNA microarray chip for measuring expression of all, or essentially all, the members of the PGS set forth in Table 1. Such custom DNA microarray chips are commercially available.

EXAMPLES

The invention is further illustrated by the following examples. The examples are provided for illustrative purposes only, and are not to be construed as limiting the scope or content of the invention in any way.

Example 1

Murine Tumor Responses to Tivozanib

A population of more than 100 murine breast tumors (BH archive) was used to identify tumors that are sensitive to tivozanib (responders) and tumors that are resistant to tivozanib (non-responders). The BH archive was established by in vivo propagation and cryopreservation of primary tumor material from more than 100 spontaneous murine breast tumors derived from engineered chimeric mice that develop Her2-dependent, inducible spontaneous breast tumors. The mice were produced essentially as follows.

Ink4a homozygous null ES cells were co-transfected with the following four constructs, as separate fragments: MMTV-rtTA, TetO-Her2$^{V664Eneu}$, TetO-luciferase and PGK-puromycin. Puromycin-resistant cells were genotyped by PCR and Southern blot. Inducibility of the oncogenes in ES cells was analyzed by northern blot. The transfected ES cells were injected into C57BL/6 blastocysts, which were transplanted into pseudo-pregnant female mice for gestation leading to birth of the chimeric mice.

The mouse mammary tumor virus long terminal repeat (MMTV) was used to drive breast-specific expression of the reverse tetracycline transactivator (rtTA). The rtTA provided for breast-specific expression of the Her2 activated oncogene, when doxycycline was provided to the mice in their drinking water.

Inducibility of the Her2 oncogene and luciferase was confirmed by RT-PCR and luciferase assay, respectively, using cultured cells derived from the mouse. Mammary glands were removed from chimeric mice and digested with collagenase. Half of the organoids collected were cultured in the presence of doxycycline, and the other half was cultured without doxycycline. After five days in culture, the cells were trypsinized, and one tenth of the cells were used for luciferase assay, and the rest were used for RNA extraction.

The histology analysis of tumors harvested from HER2 breast cancer model mice showed invasive adenocarcinomas. Two major patterns were distinguished. They were a solid sheet growth pattern, and a nested growth pattern with necrotic centers. Immunohistochemistry analysis of the mammary tumors revealed two cell types within the tumors. The first cell type was epithelial origin (cytokeratin positive), and showed HER2 expression and strong proliferation. The second cell type was mesenchymal origin with fibroblast-like appearance. These cells were collagen positive, did not show strong proliferation, and displayed stromal function. Apoptosis was seen in the necrotic centers of the epithelial part of the tumors. Tumor regression studies (regression in response to withdrawal of doxycycline) were performed to confirm that the murine model tumors were dependent on Her2 expression. Following induction of the tetracycline-responsive promoter by doxycycline, the mice developed mammary tumors with a latency of about 2 to 4 months.

Tumor cells were isolated by physical disruption of the tumors using cell strainers. Typically $1 \times 10^5$ cells were mixed with matrigel (50:50 volume) and injected subcutaneously into female NCr nu/nu mice on upper dorsal region between the shoulder blades. When these tumors grew to approximately 500 mm$^3$, which typically required 2 to 4 weeks, they were collected for further propagation, drug response testing, and analysis. Analysis included microarray profiling, general histopathology, and IHC (CD31 for tumor vasculature, Ki67 for tumor cell proliferation). The characterization of this tumor population revealed a remarkable degree of variation in key parameters of angiogenesis such as microvasculature, VEGF expression and specific gene expression profiles.

Evaluation of tumor response to tivozanib was performed essentially as follows. Subcutaneously transplanted tumors were established by injecting physically disrupted tumor cells (mixed with Matrigel) into 7 week-old female NCr nude mice. When the tumors reached approximately 200-400 mm$^3$, 30 tumor-bearing mice were randomized into three groups. Group 1 received vehicle. Group 2 received tivozanib at 5 mg/kg daily by oral gavage. Group 3 received tivozanib at 20 mg/kg daily by oral gavage. Tumors were measured twice per week by a caliper, and tumor volume was calculated. At the end of the treatment, tumors were collected for histopathological analysis and IHC analysis.

These studies revealed significant tumor-to-tumor variation in response to tivozanib. Based on tumor growth inhibition and typical histopathological and IHC (CD31) characteristics for angiogenesis inhibition, responders and non-responders were identified. Typically, responders exhibited (by histology) no tumor progression by caliper measurement and close to complete tumor killing, except the peripheries, when treated with 5 mg/kg tivozanib. The variation in response was expected, because the mouse model tumors had arisen spontaneously, and therefore they were expected to contain differing sets of random mutations that had led to tumorigenesis, including tumor angiogenesis. Such variation in response was desirable, because it was similar to the variation in naturally occurring human tumors, and thus enabled identification of tivozanib-responsive tumors and tivozanib-resistant tumors for use in identifying the molecular signature or tivozanib responsiveness.

Example 2

Identification of Differentially Expressed Genes

Messenger RNA (approx. 6 μg) from each tumor in the BH archive was subjected to an amplification protocol and hybridized using a custom Agilent microarray (Agilent mouse 40K chip). Comparison of the gene expression profile of a mouse tumor sample to control sample (universal mouse reference RNA from Stratagene, cat. #740100-41) was performed using conventional, commercially available microarray technology. Commercially available feature extraction software (Agilent Technologies, Santa Clara, Calif.) was used for feature extraction and data normalization.

Differentially expressed genes were identified when five responder tumors from the BH archive were compared against six non-responder tumors from the BH tumor archive. Conventional microarray technology was used to measure the expression of approximately 40,000 genes in samples representing each of the eleven tumors. This was done using a custom mouse 40K chip and feature extraction software, both from Agilent Technology (Santa Clara, Calif.). Statistical significance of differences in mean expression (responders versus non-responders) of each gene was evaluated through the Student's t test. The 280 genes showing the largest difference in expression level (smallest p values) were identified and associated with particular signaling pathways. This was done using commercially available software (Ingenuity Pathway Analysis Tool, Ingenuity Systems Inc., Redwood City, Calif.). Statistically significant increases in gene expression representing five pathways was observed: (1) virus entry via endocytic pathway, (2) lymphotoxin β receptor signaling pathway, (3) macropinocytosis pathway, (4) chemokine signaling pathway, and (5) Reelin signaling pathway in neurons. Three of these five upregulated pathways are involved in immune response and cytokine pathways. Therefore, these pathways were the focus of subsequent bioinformatics analyses to identify a PGS in human tumor samples.

Example 3

Identification of PGS

In view of the pathway analysis of the murine microarray data (above), we chose 16 hematopoietic marker genes (CCL2, CCL7, CCR1, CCR2, CCR3, CCR5, CCR6, CSF1R, CSF2RA, CSF2RB, CXCR4, IL3RA, IL8RA, IL8RB, and KIT) for a correlation analysis involving gene expression profiling datasets. In other words, each of the 16 hematopoietic marker genes was used separately as a reference gene for the correlation analysis, i.e., correlation of expression levels.

This information was then used to survey gene expression profiling datasets to identify a set of genes predictive of tumor responsiveness to tivozanib. We decided to use human gene expression profiling datasets, even though pathway analysis leading to the selection of hematopoietic marker genes as the correlation reference genes was done with murine data. The rationale for this was that: (1) correlated expression would be likely to reflect biological function, which would be comparable in mouse and human; and (2) the objective was to identify human biomarkers. Seven human gene expression profiling data sets related to seven different human tumors were available for the correlation analysis (Table 2).

TABLE 2

| Tumor Type | No. of Tumors in Data Set | Source of Data Set |
| --- | --- | --- |
| breast | 295 | NKI (Van de Vijver et al., 2002, N. Engl. J. Med. 347:1999-2009) |
| colon | 74 | Purchased from GeneLogic |
| kidney | 70 | Purchased from GeneLogic |
| lung | 112 | Purchased from GeneLogic |
| pancreas | 65 | Purchased from GeneLogic |
| stomach | 43 | Purchased from GeneLogic |
| glioblastoma | 326 | The Cancer Genome Atlas Research Network (2008, Nature 455:1061-1068) |

For each hematopoietic marker gene (reference gene), the correlation coefficient was calculated for each of the approximately 30,000 genes queried for each tumor represented in the seven human datasets (30K genes×985 tumors×16 hematopoietic marker genes=approx. 472,800,000 correlation coefficients). For a given reference gene, approximately 200 genes with the highest correlation coefficient ranking across the seven datasets were identified as coherently expressed genes. The rationale being that if a set of genes correlates with a given reference gene, they necessarily correlate with each other. To make a more robust and comprehensive analysis, the correlation was calculated with respect to 16 different reference genes (i.e., CCL2, CCL7, CCR1, CCR2, CCR3, CCR5, CCR6, CSF1R, CSF2RA, CSF2RB, CXCR4, IL3RA, IL8RA, IL8RB, and KIT).

This analysis revealed that co-correlation of expression across the seven human datasets was notably higher for 8 out of the 16 hematopoietic marker (reference) genes. Therefore, further analysis was limited to those 8 hematopoietic marker genes, i.e., CCL2, CCR1, CCR2, CCR5, CSF1R, CSF2RA, CSF2RB, and CSF3R. These eight 200-gene lists (one 200-gene list for each of the 8 marker genes) were compared, and these eight 200-gene lists were found to have 42 genes in common. This set of 42 genes was identified as a candidate PGS for human tumor response to tivozanib. The PGS score (average expression value of the 42 genes) was calculated according to the following equation:

$$PGS.\text{score} = \frac{1}{42} * \sum_{i=1}^{42} Ei$$

wherein $E_1, E_2, \ldots, E_{42}$ are the expression values of the 42 genes for one sample.

In other words, PGS score of a given sample is the average expression value of these 42 genes in the sample.

Example 4

Predicting Murine Response

The predictive power of the present invention was tested using 25 tumors from a proprietary archive of primary mouse tumors in which the driving oncogene was Her2. A PGS score for each of the 25 tumors was calculated from microarray data. Each of the 25 tumors was treated with tivozanib, and then categorized as being responsive or non-responsive to the drug treatment, as described in Example 1 above. The optimum threshold PGS score was empirically determined to be 0.33, in a threshold determination analysis, using ROC curve analysis.

Figure 2:
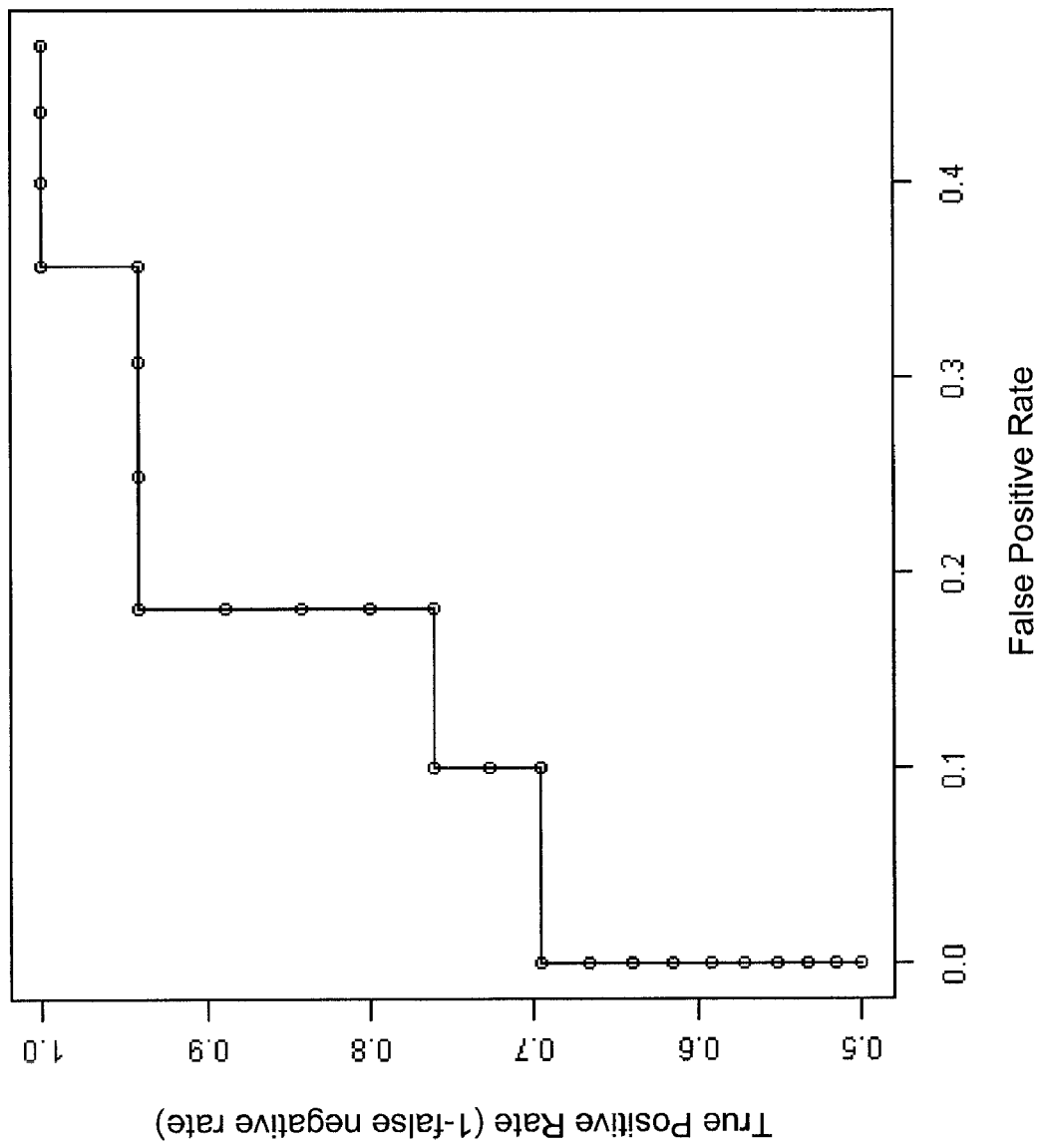
FIG. 2 is a receiver operator characteristic (ROC) curve based on the data in FIG. 1. In general, an ROC curve is used to determine the optimum threshold PGS score. The ROC curve of FIG. 2 indicates that the optimum threshold is PGS score=0.33, which yields a false positive rate of 18.2%, and a false negative rate of 5.9%.

Applying this threshold, the test yielded a correct prediction of response or non-response with regard to 22 out of the 25 tumors (FIG. 2). In predicting non-response, the false positive rate was 18.2% (2 out of 11) and the false negative rate was 5.88% (1 out of 17).

Example 5

Predicting Human Response

The following prophetic example illustrates in detail how one could use the present invention to predict human response to tivozanib, using TaqMan® data.

With regard to a given tumor type (e.g., renal cell carcinoma), tumor samples (archival FFPE blocks, fresh samples or frozen samples) are obtained from human patients (indirectly through a hospital or clinical laboratory) prior to treatment of the patients with tivozanib. Fresh or frozen tumor samples are placed in 10% neutral-buffered formalin for 5-10 hours before being alcohol dehydrated and embedded in paraffin, according to standard histology procedures.

RNA is extracted from 10 μm FFPE sections. Paraffin is removed by xylene extraction followed by ethanol washing. RNA is isolated using a commercial RNA preparation kit. RNA is quantitated using a suitable commercial kit, e.g., the RiboGreen® fluorescence method (Molecular Probes, Eugene, Oreg.). RNA size is analyzed by conventional methods.

Reverse transcription is carried out using the SuperScript™ First-Strand Synthesis Kit for qRT-PCR (Invitrogen). Total RNA and pooled gene-specific primers are present at 10-50 ng/μl and 100 nM (each) respectively.

For each gene in the PGS, qRT-PCR primers are designed using a suitable commercial software, e.g., Primer Express® software (Applied Biosystems, Foster City, Calif.). The oligonucleotide primers are synthesized using a commercial synthesizer instrument and appropriate reagents, as recommended by the instrument manufacturer or vendor. Probes are labeled using a suitable commercial labeling kit.

TaqMan® reactions are performed in 384-well plates, using an Applied Biosystems 7900HT instrument according to the manufacturer's instructions. Expression of each gene in the PGS is measured in duplicate 5 μl reactions, using cDNA synthesized from 1 ng of total RNA per reaction well. Final primer and probe concentrations are 0.9 μM (each primer) and 0.2 μM, respectively. PCR cycling is carried out according to a standard operating procedure. To verify that the qRT-PCR signal is due to RNA rather than contaminating DNA, for each gene tested, a no RT control is run in parallel. The threshold cycle for a given amplification curve during qRT PCR occurs at the point the fluorescent signal from probe cleavage grows beyond a specified fluorescence threshold setting. Test samples with greater initial template exceed the threshold value at earlier amplification cycles.

To compare gene expression levels across all the samples, normalization based on five reference genes (housekeeping genes whose expression level is assumed to be similar across all samples) is used to correct for differences arising from variation in RNA quality, and total quantity of RNA, in each assay well. A reference $C_T$ (threshold cycle) for each sample is defined as the average measured $C_T$ of the reference genes. Normalized mRNA levels of test genes are defined as $\Delta C_T +10$, where $\Delta C_T$=reference gene $C_T$ minus test gene $C_T$.

The PGS score for each tumor sample is calculated from the gene expression levels, according to algorithm set forth above. The actual response data associated with tumor sample tested are obtained from the hospital or clinical laboratory supplying the tumor samples. Clinical response is typically is defined in terms of tumor shrinkage, e.g., 30% shrinkage, as determined by suitable imaging technique, e.g., CT scan. In some cases, human clinical response is defined in terms of time, e.g., progression free survival time. The optimal threshold PGS score for the given tumor type is calculated, as described above. Subsequently, this optimal threshold PGS score is used to predict whether newly-tested human tumors of the same tumor type will be responsive or non-responsive to treatment with tivozanib.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

The invention claimed is:

1. A method of identifying a human tumor as likely to be responsive or non-responsive to treatment with tivozanib, comprising:
   (a) measuring, in a sample from the human tumor, the relative expression level of each gene in a predictive gene set (PGS), wherein the PGS consists of the following genes:
   AIF1, APBB1IP, ARHGAP30, C3AR1, CCR1, CD37, CD53, CD86, CLEC7A, CSF1R, CSF2RB, CTSS, CYBB, DOCK2, EVI2A, EVI2B, FPR3, GMFG, GPR65, HCK, HCLS1, HLA-DMA, IL10RA, ITGB2, LAIR1, LCP1, LCP2, LILRB1, LILRB2, LST1, LY86, MNDA, MS4A6A, MYO1F, NCF4, SLA, SLAMF8, TLR1, TYROBP, PLEK, CYTH4, and PTPRC; and
   (b) calculating a PGS score according to the algorithm $$PGS.\text{score} = \frac{1}{42} * \sum_{i=1}^{42} Ei$$

wherein $E_1, E_2, \ldots E_{42}$ are the expression values of the 42 genes in the PGS, and
   wherein a PGS score below a defined threshold indicates that the tumor is likely to be responsive to tivozanib, and a PGS score above the defined threshold indicates that the tumor is likely to be resistant to tivozanib.

2. The method of claim 1, further comprising the step of performing a threshold determination analysis, thereby generating a defined threshold, wherein the threshold determination analysis comprises a receiver operator characteristic curve analysis.

3. The method of claim 1, wherein the relative expression level of each gene in the PGS is measured by DNA microarray analysis.

4. The method of claim 1, wherein the relative expression level of each gene in the PGS is measured by qRT-PCR analysis.

5. A PCR primer set consisting of a pair of primers for each of the following genes:
   A1F1, APBB1IP, ARHGAP30, C3AR1, CCR1, CD37, CD53, CD86, CLEC7A, CSF1 R, CSF2RB, CTSS, CYBB, DOCK2, EVI2A, EVI2B, FPR3, GMFG, GPR65, HCK, HCLS1, HLA-DMA, IL10RA, ITGB2, LAIR1, LCP1, LCP2, LILRB1, LILRB2, LST1, LY86, MNDA, MS4A6A, MYO1F, NCF4, SLA, SLAMF8, TLR1, TYROBP, PLEK, CYTH4, and PTPRC.

6. A DNA microarray chip consisting of a solid surface and a probe set, said probe set consisting of probes specific for each of the following genes:
   AIF1, APBB1IP, ARHGAP30, C3AR1, CCR1, CD37, CD53, CD86, CLEC7A, CSF1R, CSF2RB, CTSS, CYBB, DOCK2, EVI2A, EVI2B, FPR3, GMFG, GPR65, HCK, HCLS1, HLA-DMA, IL10RA, ITGB2, LAIR1, LCP1, LCP2, LILRB1, LILRB2, LST1, LY86, MNDA, MS4A6A, MYO1F, NCF4, SLA, SLAMF8, TLR1, TYROBP, PLEK, CYTH4, and PTPRC.

* * * * *